United States Patent
Sakkani et al.

(10) Patent No.: US 11,465,988 B2
(45) Date of Patent: Oct. 11, 2022

(54) PROCESS FOR THE PREPARATION OF TIPIRACIL HYDROCHLORIDE AND INTERMEDIATES THEREOF

(71) Applicant: NATCO PHARMA LIMITED, Hyderabad (IN)

(72) Inventors: Srinivasulu Sakkani, Hyderabad (IN); Uma Naresh Babu Kotra, Hyderabad (IN); Dharmender Ragidi, Hyderabad (IN); Buchappa Gongalla, Hyderabad (IN); Durga Prasad Konakanchi, Hyderabad (IN); Pulla Reddy Muddasani, Hyderabad (IN); Venkaiah Chowdary Nannapaneni, Hyderabad (IN)

(73) Assignee: NATCO PHARMA LIMITED, Hyderabad (IN)

( * ) Notice: Subject to any disclaimer, the term of this patent is extended or adjusted under 35 U.S.C. 154(b) by 0 days.

(21) Appl. No.: 17/418,752

(22) PCT Filed: Dec. 13, 2019

(86) PCT No.: PCT/IN2019/050914
§ 371 (c)(1),
(2) Date: Jun. 25, 2021

(87) PCT Pub. No.: WO2020/121334
PCT Pub. Date: Jun. 18, 2020

(65) Prior Publication Data
US 2022/0056016 A1     Feb. 24, 2022

(30) Foreign Application Priority Data
Dec. 15, 2018   (IN) .............................. 201841047514

(51) Int. Cl.
*C07D 403/06* (2006.01)
*C07D 207/22* (2006.01)
*C07D 239/553* (2006.01)

(52) U.S. Cl.
CPC ......... *C07D 403/06* (2013.01); *C07D 207/22* (2013.01); *C07D 239/553* (2013.01)

(58) Field of Classification Search
CPC . C07D 403/06; C07D 207/22; C07D 239/553
See application file for complete search history.

(56) References Cited

U.S. PATENT DOCUMENTS

| | | |
|---|---|---|
| 4,699,918 A | 10/1987 | Maillard et al. |
| 5,744,475 A | 4/1998 | Yano et al. |

FOREIGN PATENT DOCUMENTS

| | | | |
|---|---|---|---|
| CN | 103980253 A | | 8/2014 |
| CN | 106632081 A | | 5/2017 |
| CN | 106892902 A | * | 6/2017 |
| WO | WO 2019/049174 | * | 3/2019 |

OTHER PUBLICATIONS

Callahan et al., Identification of Novel Inhibitors of the Transforming Growth Factor β1 (TGF-β1) Type 1 Receptor (ALK5), J. Med. Chem., 45(5), pp. 999-1001 (2002) JM010493Y; including Supporting Information of 11 pages.*
CN 103980253 A (machine translation by Espacenet) 8 pages (2014).*
CN 106892902 A (machine translation by Espacenet) 10 pages (2017).*
International Search Report dated Mar. 17, 2020 in related PCT Application No. PCT/IN2019/050914, 1 page.
Petersen et al., "Reactions of cyclic lactim ethers with acylated hydrazine derivatives," Chem. Ber., 1957, 90, 909 to 921.
Shridhar et al., "Synthesis & Hypoglycemic Activity of Some New Arylsulphonylurea Derivatives of Cyclic Amidines," Indian J. Chem. B, 1985, 24B(6), 693 to 694.
Yano, Shingo et al., "Synthesis and evaluation of 6-methylene-bridged uracil derivatives. Part 2: Optimization of inhibitors of human thymidine phosphorylase and their selectivity with uridine phosphorylase," Bioorg. Med. Chem., 2004, 12, 3443 to 3450.

* cited by examiner

*Primary Examiner* — Deepak R Rao
(74) *Attorney, Agent, or Firm* — Kilpatrick Townsend & Stockton LLP

(57) ABSTRACT

The present invention provides a process for the preparation of Tipiracil HCl of Formula (I) and intermediate thereof with improved yields and purities.

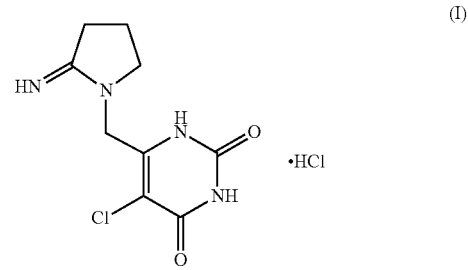

(I)

8 Claims, No Drawings

PROCESS FOR THE PREPARATION OF TIPIRACIL HYDROCHLORIDE AND INTERMEDIATES THEREOF

FIELD OF THE INVENTION

The present invention relates to an improved process for preparation of Tipiracil hydrochloride of Formula (I) and intermediates thereof.

Formula (I)

BACKGROUND OF THE INVENTION

Tipiracil hydrochloride is chemically known as 5-chloro-6-[(2-iminopyrrolidin-1-yl)methyl]pyrimidine-2,4-(1H,3H)-dione or 2,4-(1H,3H)-pyrimidinedione-5-chloro-6-[(2-imino-1-pyrrolidinyl)methyl], hydrochloride (1:1) of Formula (I). Tipiracil hydrochloride has an inhibitory action on human thymidine phosphorylase and an enhancing action on the antitumor effect of Trifluridine. An antitumor agent "TAS-102" composed of a mixture of Trifluridine and Tipiracil hydrochloride with a molar ratio of 1 to 0.5. Combination of Trifluridine and Tipiracil hydrochloride was approved in 2016 by EMEA and also approved in 2015 by USFDA. It is marketed in the form of oral tablets under the brand name Lonsurf® by Taiho Pharma. U.S. Pat. No. 5,744,475 discloses Tipiracil and its pharmaceutically acceptable salts.

U.S. Pat. No. 5,744,475 discloses a process for the preparation of Tipiracil hydrochloride of Formula (I) by reaction of 6-(chloromethyl)uracil of Formula (II) with sulfuryl chloride in acetic acid to produce 5-chloro-6-chloromethyluracil of Formula (III). Further, compound of Formula (III) is reacted with 2-iminopyrrolidine of Formula (IV) in the presence of sodium ethoxide base in N,N-dimethylformamide solvent followed by treating with HCl to produce Tipiracil Hydrochloride of Formula (I).

The synthetic procedure is illustrated as in Scheme-I below:

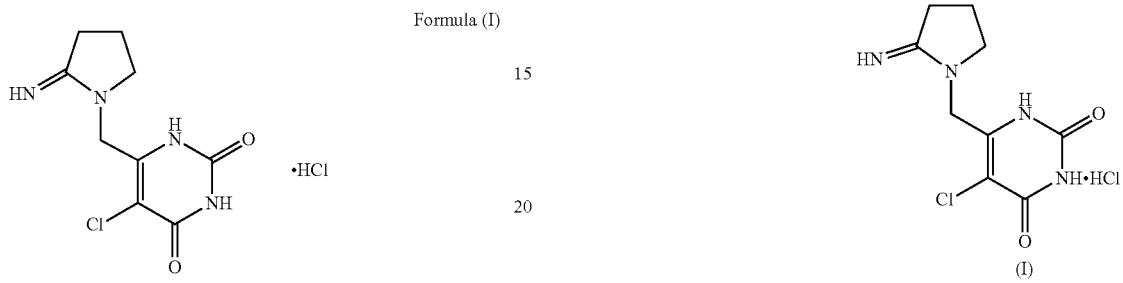

The process disclosed in U.S. Pat. No. 5,744,475 suffers from the following disadvantages outlined below:

Step-I: chlorination on 6-(chloromethyl)-2,4(1H,3H)-pyrimidinedione
  (i) Purity of compound of Formula (III) obtained in step-I is 95% (Reference: Referential Example-01 of US '475);
  (ii) Yield of compound of Formula (III) obtained in step-I is 92%. (Reference: Referential Example-01 of US '475);

Step-II: coupling of 5-chloro-6-chloromethyluracil with 2-iminopyrrolidine hydrochloride.
  (i) No purity/impurity profile is disclosed in the process.
  (ii) For isolation of the product, solvent distillation process is required, which is not capable to remove impurities.
  (iii) Overall yield of Tipiracil hydrochloride produced with the above disclosed process is only 38% (Reference: Example-06)
  (iv) Purity of Tipiracil Hydrochloride compound of Formula (I) obtained in step-II is 95%.

Shingo Yano et al., (*Bioorganic & Medicinal Chemistry* 2004, 12, 3443-3450) disclosed a process for the preparation of Tipiracil hydrochloride of Formula (I) by reaction of 4-chlorobutanenitrile of Formula-(V) with ammonia in methanol to produce 2-iminopyrrolidine hydrochloride of Formula (IVa), which is further reacted with 5-chloro-6-chloromethyluracil of Formula (III) in presence of 1,8-Diazabicyclo(5.4.0)undec-7-ene (DBU) base followed by treating with Aq.HCl to produce Tipiracil HCl of Formula (I).

The synthetic procedure is illustrated in Scheme-II as below:

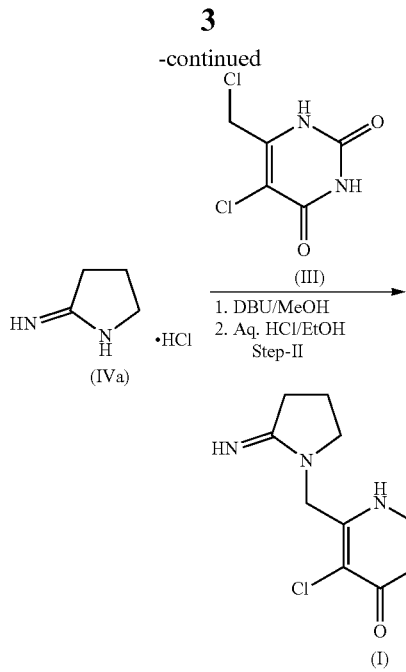

The process disclosed in *Bioorganic & Medicinal Chemistry* 2004, 12, 3443-3450 suffers from the following disadvantages outlined below:

Step-I: Synthesis of 2-iminopyrrolidine hydrochloride by using 4-chlorobutyro nitrile and ammonia
  (i) This step performed at temperature 100-120° C. in a sealed tube under pressure of ammonia, which is not viable in commercial scale.
  (ii) Expensive 4-chlorobutyronitrile of Formula (V) is used in the process which is not viable on commercial scale.
  (iii) No purity/impurity profile is disclosed in the process.

Step-II: Coupling of 5-chloro-6-chloromethyluracil with 2-iminopyrrolidine hydrochloride
  (i) Expensive reagent DBU is used in the process which is not viable on commercial scale.
  (ii) Impurity profile is not disclosed in the process.
  (iii) Purity of Tipiracil Hydrochloride compound of Formula (I) obtained in step-II is 95%. (Reference: page no 3450 and paragraph: 5.1.24)

Petersen et al., (*Chemische Berichte*, 90, 909-21; 1957) and Shridhar et al., (*Indian Journal of Chemistry, Section B: Organic Chemistry Including Medicinal Chemistry*, 1985, 24B(6), 693-4) disclosed a process for the preparation of 2-iminopyrrolidine hydrochloride of Formula (IVa) by reaction of 2-pyrrolidinone of Formula (VI) with dimethyl sulfate in benzene to produce 2-methoxy-1-pyrroline of Formula (VII), which is further reacted with ammonium chloride in ethanol to produce 2-iminopyrrolidine hydrochloride of Formula (IVa).

The synthetic procedure is illustrated in Scheme-III as below:

Scheme-III

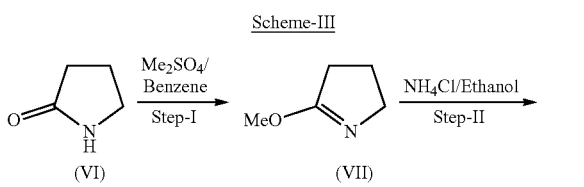

The process disclosed in *Chemische Berichte*, 90, 909-21; 1957 and *Indian Journal of Chemistry, Section B: Organic Chemistry Including Medicinal Chemistry*, 1985, 24B(6), 693-4 suffers from the following disadvantages outlined below:
  (i) Class-1 solvent Benzene (carcinogenic solvent) is used in the process;
  (ii) No purity/impurity profile is disclosed in the process.
  (iii) Purification method is not given.

Hence, there exists a need to have simple, scalable, easy to handle and cost effective process for the preparation of Tipiracil HCl of Formula (I) and intermediate thereof with high chemical purity and high yield.

OBJECTIVE OF THE INVENTION

The main objective of the present invention is to provide a simple and cost effective process for the preparation of Tipiracil HCl of Formula (I) and intermediate thereof with high purity and good yield on a commercial scale.

SUMMARY OF THE INVENTION

The present invention provides an improved process for the preparation of Tipiracil HCl of Formula (I), Formula (I)

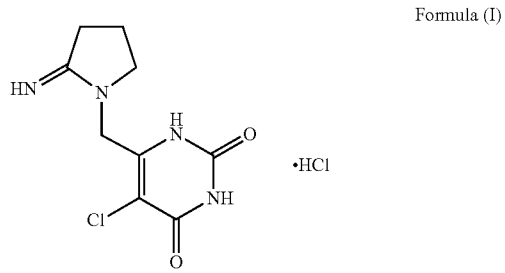 [SMILES: N=C1CCCN1Cc1[nH]c(=O)[nH]c(=O)c1Cl ; Cl]

comprising the steps of:
a) reacting 5-chloro-6-chloromethyluracil of Formula (III), Formula (III)

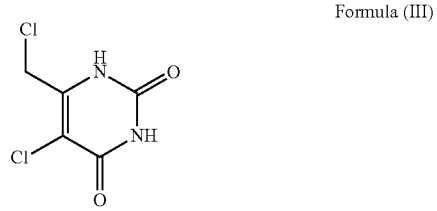 [SMILES: O=c1[nH]c(CCl)c(Cl)c(=O)[nH]1]

with 2-iminopyrrolidine hydrochloride of Formula (IVa)

Formula (IVa)

in presence of sodium methoxide in a solvent to produce Tipiracil free base of Formula (Ia).

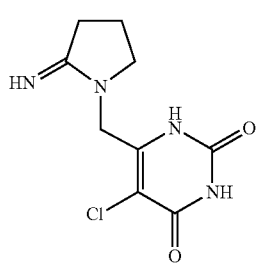

Formula (Ia)

b) treating the Tipiracil free base of Formula (Ia) with hydrochloric acid to produce Tipiracil HCl of Formula (I).
c) purifying the Tipiracil HCl of Formula (I) from a ketone solvent.
wherein the obtained Tipiracil HCl of Formula (I) has
a) more than 99.5% of purity; and
b) more than 65% of overall yield.

The present invention further provides a process for preparation of 5-chloro-6-chloromethyluracil of Formula (III),

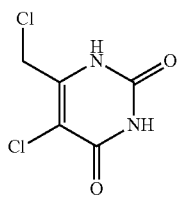

Formula (III)

comprising the steps of:
a) reacting 6-(chloromethyl)uracil of Formula (II),

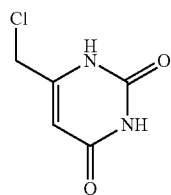

Formula (II)

with sulfuryl chloride in the presence of acetic acid to produce 5-chloro-6-chloromethyluracil of Formula (III).
b) purifying the 5-chloro-6-chloromethyluracil of Formula (III) from a suitable solvent.

The present invention further provides a process for preparation of 2-iminopyrrolidine hydrochloride of Formula (IVa),

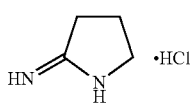

Formula (IVa)

comprising the steps of:
a) reacting 2-Pyrrolidone of Formula (VI),

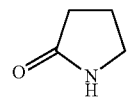

Formula (VI)

with dimethyl sulfate to produce 2-methoxy-1-pyrroline of Formula (VII)

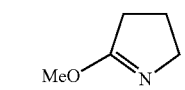

Formula (VII)

b) reacting the compound of Formula (VII) in-situ with ammonium chloride in a suitable solvent to produce 2-iminopyrrolidine hydrochloride of Formula (IVa).

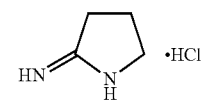

Formula (IVa)

c) purifying the 2-iminopyrrolidine hydrochloride of Formula (IVa) from a solvent selected from alcohol or ketone or a mixture thereof.

DETAILED DESCRIPTION OF THE INVENTION

The present invention provides an improved process for the preparation of Tipiracil HCl of Formula (I), comprising the steps of:
a) reacting 5-chloro-6-chloromethyluracil of Formula (III) with 2-iminopyrrolidine hydrochloride of Formula (IVa) in presence of sodium methoxide in a solvent to produce Tipiracil free base of Formula (Ia).
b) treating the Tipiracil free base of Formula (Ia) with hydrochloric acid to produce Tipiracil HCl of Formula (I).
c) purifying the Tipiracil HCl of Formula (I) from a ketone solvent.
wherein the obtained Tipiracil HCl of Formula (I) has
a) more than 99.5% of purity; and
b) more than 65% of overall yield.

The solvent used in step a) is selected from an alcoholic solvent such as methanol, ethanol, n-propanol, isopropanol, n-butanol, isobutyl alcohol, tert-butyl alcohol, isoamyl alcohol, 2-methoxyethanol or mixture thereof preferably methanol; a ketone solvent such as acetone, methyl isobutyl ketone, 2-pentanone, ethyl methyl ketone, diethyl ketone; esters such as ethyl acetate, methyl acetate, butyl acetate, isopropyl acetate, 2-methoxyethyl acetate; a polar solvent such as N,N-dimethylformamide, dimethyl sulfoxide, acetonitrile, dichloromethane, or mixture thereof preferably N,N-dimethylformamide.

In step (a), the reaction may be performed from 20° C. to 45° C. for 15 hours to 30 hours, preferably 15-25° C. for 19 hours to 20 hours. The obtained Tipiracil free base (Ia) may be used in the next reaction directly or optionally after further purification.

In step (b), in situ or isolated Tipiracil free base obtained from step (a) is treated with aqueous hydrochloric acid to produce Tipiracil hydrochloride of Formula (I). The reaction may be performed from 50° C. to 70° C. for 1-4 hours, preferably 60° C. to 65° C. for 1-2 hours.

In step (c), solvent used for purification of Tipiracil hydrochloride is selected from a ketone solvent such as acetone, methyl ethyl ketone, methyl isobutyl ketone, methyl amyl ketone or mixture thereof. The purification may be performed from 25° C. to 65° C. for 1 hour to 4 hours, preferably 46-53° C. In step (c) the HPLC purity of Tipiracil HCl of Formula (I) obtained after purification process is 99.8%.

The present invention further provides a process for preparation of 5-chloro-6-chloromethyluracil of Formula (III), comprising the steps of:

(a) reacting 6-(chloromethyl)uracil of Formula (II), with sulfuryl chloride in the presence of acetic acid solvent to produce 5-chloro-6-chloromethyluracil of Formula (III), (b) purifying the 5-chloro-6-chloromethyluracil of Formula (III) from a suitable solvent.

In step (a) the reaction may be performed from 10° C. to 40° C. for 5 hours to 10 hours, preferably 15-25° C. for 4 hours to 6 hours.

In step (b) suitable solvent is selected from DMF, methanol, water or mixture thereof. Temperature of purification process may be from 15° C. to 40° C. for 1 hour to 4 hours, preferably 25-35° C. for 1 hours to 2 hours.

The present invention further provides a process for preparation of 2-iminopyrrolidine hydrochloride of Formula (IVa), comprising the steps of:

(a) reacting 2-pyrrolidone of Formula (VI), with dimethyl sulfate to produce 2-methoxy-1-pyrroline of Formula (VII), (b) reacting compound of Formula (VII) in-situ with ammonium chloride in a suitable solvent to produce 2-iminopyrrolidine hydrochloride of Formula (IVa), (c) purifying the 2-iminopyrrolidine hydrochloride of Formula (IVa) from a solvent selected from alcohol or ketone or a mixture thereof.

In step (a) the reaction may be performed from 25° C. to 70° C. for 2 to 6 hours, preferably 2-3 hrs at 60° C.-65° C. The obtained 2-methoxy-1-pyrroline of Formula (VII) may be used in the next step directly.

In step (b) suitable solvent is selected from dichloromethane, toluene, methyl tertiary-butyl ether (MTBE), methanol, ethanol, 1-propanol or mixture thereof.

In step (c) alcohol solvent is selected from an alcohol such as methanol, ethanol, 1-propanol, isopropanol, tert-butyl alcohol, isoamyl alcohol, 2-methoxyethanol or mixture thereof, preferably, methanol; ketone solvent such as acetone, methyl ethyl ketone, methyl iso butyl ketone and methyl amyl ketone or mixture thereof. The reaction may be performed from 20° C. to 45° C. for 5 to 15 hours, preferably 11-15 hrs at 25-35° C. The obtained 2-iminopyrrolidine hydrochloride of Formula (IVa) may be used in the next reaction directly or optionally after further purification. 2-iminopyrrolidine hydrochloride of Formula (IVa) is leached from 7.5% methanolic acetone. HPLC purity of 2-iminopyrrolidine hydrochloride of Formula (IVa) obtained after purification process is above 99.8%

Advantages of Present Invention

In the preparation of 5-chloro-6-chloromethyluracil of Formula (III):
1. Impurities formation is controlled by reducing reaction maintenance temperature (15-25° C.).
2. Purification method is developed and achieved 99.2% purity
3. Purity of the compound of Formula (III) is improved to above 99% from literature yield of 92%.

In the process for preparation of 2-iminopyrrolidine hydrochloride of Formula (IVa):
1. Dichloromethane (DCM) is used as solvent to avoid workup problems.
2. Compound of Formula (III) is isolated by adding acetone to reaction mass followed by filtration to obtain 72% yield with 99.8% purity.

In the process for the preparation of pharmaceutical grade Tipiracil hydrochloride:
1. Inexpensive sodium methoxide is used as base.
2. Product isolation and purification process is modified and achieved 85% yield with 99.9% purity.

The following examples are provided to illustrate the invention and are merely for illustrative purpose only and should not be construed to limit the scope of the invention.

EXAMPLES

Example-1: Process for the Preparation of 2-Iminopyrrolidine Hydrochloride of Formula (IVa)

2-Pyrrolidone (50 g) was charged into a well cleaned and oven dried 1 L 4 neck RB flask. Dimethyl sulfate (81.5 g) was added slowly to the reaction mass at 30±5° C. in about 20-30 min and stirred at 30±5° C. for 20-30 min. The reaction mass temperature was raised to 62.5±2.5° C. and maintained for 2-3 h. After TLC compliance, the reaction mass was cooled to 5±5° C. DM water 50 mL was added slowly to the reaction mass at 5±5° C. in about 20-30 min. Methylene chloride (100 mL) was added slowly to the reaction mass at 5±5° C. in about 20-30 min. TEA (67.0 g) was added to the reaction mass at 5±5° C. in about 20-30 min and maintained the reaction mass at 5±5° C. for 20-30 min. The reaction mass temperature was raised to 30±5° C. and separated aqueous and organic layers. Aqueous layer was extracted twice with methylene chloride. Organic layers were combined and washed with saturated sodium chloride solution. Organic layer was transferred into a well cleaned and dried 1 L 4N RBF and ammonium chloride 28.3 g was charged into it. The reaction mass was stirred at 30±5° C. for 11-12 h. After QTLC compliance, acetone solvent was added slowly (300 mL) to the reaction mass at 30±5° C. in about 20-30 min (to avoid lump formation). The reaction mass was filtered and purified in methanol and acetone mixture to obtained 2-iminopyrrolidine hydrochloride as white crystalline powder. Yield: 72%; Purity: 99.8%

Example-2: Process for the Preparation of 5-Chloro-6-Chloromethyluracil of Formula (III)

Acetic acid (150 ml) was charged into a well cleaned and oven dried 500 mL 4 neck RB flask, and 50 g of 6-(chloromethyl)uracil of Formula (II) was added. The reaction mass temperature was cooled to 20±5° C. and added 73.59 g of sulfuryl chloride in about 30-45 min. The reaction mass was stirred for 4-5 h at 20±5° C. After consumption of the reaction, the reaction mass was cooled to 5±5° C. 200 mL of DM Water was added at 5±5° C. and maintained the reaction mass for 20-30 min. Filtered the product under vacuum, washed with DM Water followed by methanol. Crude Yield: 83% with 95% purity The wet material was transferred into a 500 mL 4 neck RB flask and 300 mL of DMF was charged into it. The reaction mass was stirred for 10-15 min at 30±5° C. 2.5 g of activated carbon was added to the reaction mass and stirred for 20-30 min at 30±5° C. The carbon was filtered and washed with 25 mL of DMF. The filtrate was transferred the into a 1 L 4 neck RB flask and 290 mL of DM Water was added at 30±5° C. Solid formation was observed during the addition of water. The reaction mass was stirred for 20-30 min at 30±5° C. and filtered the reaction mass under vacuum. The reaction mass was washed with DM Water, followed by methanol, suck dried thoroughly. The wet compound was dried to obtain 5-chloro-6-chloromethyluracil of Formula (III) as white crystalline powder with 99.2% purity. Yield: 82%.

Example-3: Process for the Preparation of Crude Tipiracil HCl of Formula (I)

5-chloro-6-chloromethyluracil of Formula (III) (75 g), 2-iminopyrrolidine hydrochloride of Formula (IVa) (92.75 g), and dimethylformamide (DMF) (750 ml) were charged in to a well cleaned and oven dried 2.0 L 4 neck RB flask under stirring. Cream colored suspension formation was observed. The reaction mass was stirred for 5-10 min at 30±5° C. followed by cooled to 20° C. 62.25 g of sodium methoxide powder was added to reaction mass and stirred for 19-20 h at 30±5° C. After consumption of starting material, the reaction mass was filtered into a Buchner funnel and flask, kept under vacuum. The wet cake was washed with 150 mL of dimethylformamide and suck dried for 45-60 min.

The wet cake was transferred into a 1 L 4 neck RB flask and 225 mL of DM Water was added. The reaction mass neutralised with acetic acid and filtered under vacuum followed by washed with water. The wet cake and 375 mL of aqueous HCl were transferred into a 1.0 L 4 neck RB flask and raised the mass temperature to 60-65° C. followed by checked for dissolution. 3.75 g of activated carbon was added to reaction mass and stirred for 30-45 min at 60-65° C. The reaction mass was filtered under vacuum and washed with 20 mL of DM Water. The filtrate was transferred into a 3 L 4 neck RB flask and raised the reaction mass temperature to 50±2.5° C., checked for dissolution. Clear solution formation was observed. 2.25 L of acetone was slowly added to the solution over a period of 30-45 min at 50±2.5° C. The reaction mass was cooled to 0-5° C., stirred the reaction mass at 0-5° C. for 60-90 min. The reaction mass was filtered under vacuum and washed the wet cake with acetone and suck dried for 20-30 min. The wet compound was dried to obtain technical grade Tipiracil hydrochloride as white crystalline powder with 99.0% purity. Yield: 85%.

Example-4: Process for the Purification of Crude Tipiracil HCl of Formula (I)

Crude Tipiracil HCl (55 g), DM Water (Lot-1, 275 ml) were charged in to a well cleaned and oven dried 1.0 L 4 neck RB flask, under stirring. The reaction mass temperature was raised to 57.5±2.5° C. and stirred for 10-15 min at 62.5±2.5° C. The clear solution was filtered under suction and washed with DM Water. The filtrate was transferred into 3 L 4 neck RBF. The reaction mass temperature was raised to 50±2.5° C. 1.65 L of acetone was added slowly at 50±2.5° C. in about 30-45 min. The reaction mass was cooled to 30±5° C. and stirred at 30±5° C. for 60-90 min. The reaction mass was filtered under vacuum and washed with of acetone.

The wet compound was dried to obtain Tipiracil hydrochloride as white crystalline powder with 99.8% purity and overall yield: 67%.

We claim:
1. An improved process for the preparation of Tipiracil HCl of Formula (I),

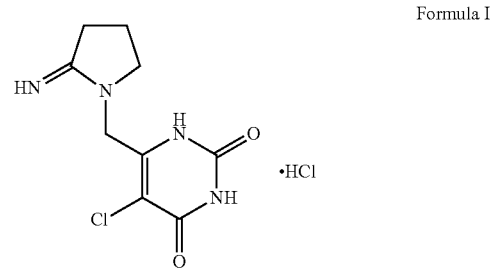 [SMILES: N=C1CCCN1Cc1[nH]c(=O)[nH]c(=O)c1Cl ; Cl]

Formula I comprising the steps of:
a) reacting 5-chloro-6-chloromethyluracil of Formula (III),

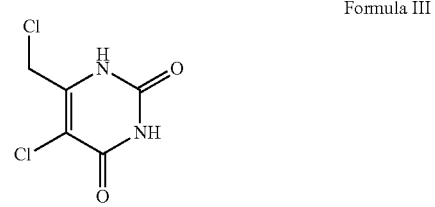 [SMILES: O=c1[nH]c(CCl)c(Cl)c(=O)[nH]1]

Formula III with 2-iminopyrrolidine hydrochloride of Formula (IVa)

Formula (IVa)

in presence of sodium methoxide in a solvent to produce Tipiracil free base of Formula (Ia),

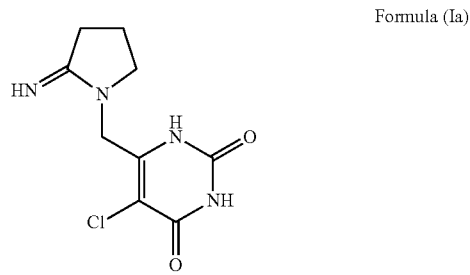 [SMILES: N=C1CCCN1Cc1[nH]c(=O)[nH]c(=O)c1Cl]

Formula (Ia)

b) treating the Tipiracil free base of Formula (Ia) with hydrochloric acid to produce Tipiracil HCl of Formula (I),
c) purifying the Tipiracil HCl of Formula (I) from a ketone solvent,
wherein the obtained Tipiracil HCl of Formula (I) has
a) more than 99.5% of purity; and
b) more than 65% of overall yield.

2. The process as claimed in claim 1, wherein the solvent used in step-(a) is selected from methanol, ethanol, n-propanol, isopropanol, n-butanol, isobutylalcohol, tert-butylalcohol, isoamyl alcohol, 2-methoxyethanol, acetone, methylisobutylketone, 2-pentanone, ethyl methyl ketone, diethyl ketone; ethyl acetate, methyl acetate, butyl acetate, isopropyl acetate, methoxy ethyl acetate, N,N-dimethylformamide, dimethylsulfoxide, acetonitrile, dichloromethane or mixture thereof.

3. The process as claimed in claim 1, where the ketone solvent used in step-(c) is selected from acetone, methyl ethyl ketone, methyl iso butyl ketone, methyl amyl ketone or mixture thereof.

4. The process as claimed in claim 1, where the 5-chloro-6-chloromethyluracil of Formula (III),

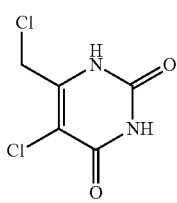

Formula III is produced according to a process comprising the steps of:
a) reacting 6-(chloromethyl)uracil of Formula (II),

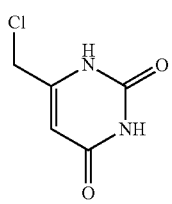

Formula (II)

with sulfuryl chloride in the presence of acetic acid solvent to produce 5-chloro-6-chloromethyluracil of Formula (III),
b) purifying the 5-chloro-6-chloromethyluracil of Formula (III) from a suitable solvent.

5. The process as claimed in claim 4, wherein the suitable solvent used in step-b) is selected from DMF, methanol and water or mixture thereof.

6. The process as claimed in claim 1, where the 2-iminopyrrolidine hydrochloride of Formula (IVa),

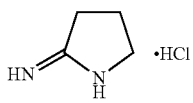

Formula (IVa)

is produced according to a process comprising the steps of:
a) reacting 2-pyrrolidinone of Formula (VI),

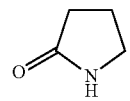

Formula (VI)

with dimethyl sulfate to produce 2-methoxy-1-pyrroline of Formula (VII)

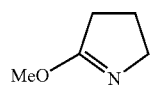

Formula (VII)

b) reacting the compound of Formula (VII) in-situ with ammonium chloride in a suitable solvent to produce 2-iminopyrrolidine hydrochloride of Formula (IVa)

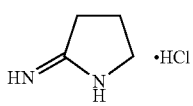

Formula (IVa)

c) purifying the 2-iminopyrrolidine hydrochloride of Formula (IVa) from a solvent selected from alcohol or ketone or a mixture thereof.

7. The process as claimed in claim 6, wherein solvent used in step-(b) is selected from dichloromethane, toluene, methyl tertiary butyl ether, methanol, ethanol, 1-propanol or mixture thereof.

8. The process as claimed in claim 6, wherein the alcohol solvent used in step-(c) is selected from methanol, ethanol, propanol, isopropanol, tert-butylalcohol, isoamyl alcohol, 2-methoxyethanol or mixture thereof; ketone solvent used in step-(c) is selected from acetone, methyl ethyl ketone, methyl iso butyl ketone, methyl amyl ketone or mixture thereof.

* * * * *